(12) United States Patent
Basir et al.

(10) Patent No.: US 11,447,138 B2
(45) Date of Patent: Sep. 20, 2022

(54) DRIVER READINESS AND INTEGRATED PERFORMANCE ASSESSMENT

(71) Applicant: IMS SOLUTIONS, INC., Schaumburg, IL (US)

(72) Inventors: Otman A. Basir, Waterloo (CA); William Ben Miners, Guelph (CA); Jason Toonstra, Elmira (CA)

(73) Assignee: Appy Risk Technologies Limited, Cheshire (GB)

( * ) Notice: Subject to any disclaimer, the term of this patent is extended or adjusted under 35 U.S.C. 154(b) by 284 days.

(21) Appl. No.: 15/507,540

(22) PCT Filed: Aug. 31, 2015

(86) PCT No.: PCT/US2015/047740
§ 371 (c)(1),
(2) Date: Feb. 28, 2017

(87) PCT Pub. No.: WO2016/033587
PCT Pub. Date: Mar. 3, 2016

(65) Prior Publication Data
US 2017/0247037 A1 Aug. 31, 2017

Related U.S. Application Data

(60) Provisional application No. 62/043,839, filed on Aug. 29, 2014.

(51) Int. Cl.
*B60W 40/08* (2012.01)
*A61B 5/18* (2006.01)
(Continued)

(52) U.S. Cl.
CPC ............. *B60W 40/08* (2013.01); *A61B 5/024* (2013.01); *A61B 5/0531* (2013.01); *A61B 5/14532* (2013.01); *A61B 5/18* (2013.01); *A61B 5/4806* (2013.01); *A61B 5/6802* (2013.01); *B60K 28/06* (2013.01); *B60W 40/06* (2013.01); *B60W 50/0097* (2013.01); *G06Q 40/08* (2013.01); *G09B 19/14* (2013.01); *G09B 19/167* (2013.01); *B60W 2040/0827* (2013.01);
(Continued)

(58) Field of Classification Search
CPC .. B60W 40/08; B60W 40/06; B60W 50/0097; A61B 5/024; A61B 5/0531; A61B 5/14532; A61B 5/18; A61B 5/4806; A61B 5/6802; B60K 28/06; G06Q 40/08; G09B 19/14; G09B 19/167
USPC .......................................................... 434/65
See application file for complete search history.

(56) References Cited

U.S. PATENT DOCUMENTS

| | | | | |
|---|---|---|---|---|
| 6,014,081 A * | 1/2000 | Kojima | .................... | G07C 5/04 340/439 |
| 6,265,978 B1 * | 7/2001 | Atlas | ...................... | G08B 21/06 340/573.1 |

(Continued)

*Primary Examiner* — Robert P Bullington
(74) *Attorney, Agent, or Firm* — Carlson, Gaskey & Olds, P.C.

(57) ABSTRACT

A driver assessment system includes at least one vehicle sensor on a vehicle gathering vehicle dynamics information. At least one occupant sensor gathers driver information. The at least one occupant sensor may be a wearable device or subdermal device on the driver. At least one computer receives the vehicle dynamics information and the driver information to determine a driver readiness.

27 Claims, 1 Drawing Sheet

(51) Int. Cl.
  *B60W 50/00* (2006.01)
  *A61B 5/024* (2006.01)
  *A61B 5/0531* (2021.01)
  *A61B 5/145* (2006.01)
  *B60K 28/06* (2006.01)
  *A61B 5/00* (2006.01)
  *B60W 40/06* (2012.01)
  *G06Q 40/08* (2012.01)
  *G09B 19/14* (2006.01)
  *G09B 19/16* (2006.01)

(52) U.S. Cl.
  CPC ............. *B60W 2040/0836* (2013.01); *B60W 2040/0872* (2013.01); *B60W 2050/0075* (2013.01); *B60W 2420/42* (2013.01); *B60W 2520/10* (2013.01); *B60W 2520/105* (2013.01); *B60W 2520/125* (2013.01); *B60W 2540/22* (2013.01); *B60W 2540/24* (2013.01); *B60W 2540/26* (2013.01); *B60W 2552/00* (2020.02); *B60W 2552/20* (2020.02); *B60W 2555/20* (2020.02); *B60W 2556/45* (2020.02); *B60W 2556/65* (2020.02); *B60W 2756/10* (2020.02)

(56) References Cited

U.S. PATENT DOCUMENTS

| | | | | |
|---|---|---|---|---|
| 6,313,749 | B1* | 11/2001 | Horne | G08B 21/06 340/575 |
| 6,661,345 | B1* | 12/2003 | Bevan | G08B 21/06 340/575 |
| 2005/0246134 | A1* | 11/2005 | Nagai | A61B 5/18 702/182 |
| 2007/0080816 | A1* | 4/2007 | Haque | B60K 28/066 340/576 |
| 2011/0022298 | A1* | 1/2011 | Kronberg | G01C 21/3484 701/532 |
| 2013/0226408 | A1* | 8/2013 | Fung | B60W 40/09 701/41 |
| 2014/0046546 | A1* | 2/2014 | Kollegger | B60W 40/09 701/41 |
| 2015/0327803 | A1* | 11/2015 | Fujita | A61B 5/11 340/576 |
| 2015/0328985 | A1* | 11/2015 | Kim | H04N 5/23229 180/272 |
| 2015/0351681 | A1* | 12/2015 | Lee | A61B 5/4806 600/595 |

* cited by examiner

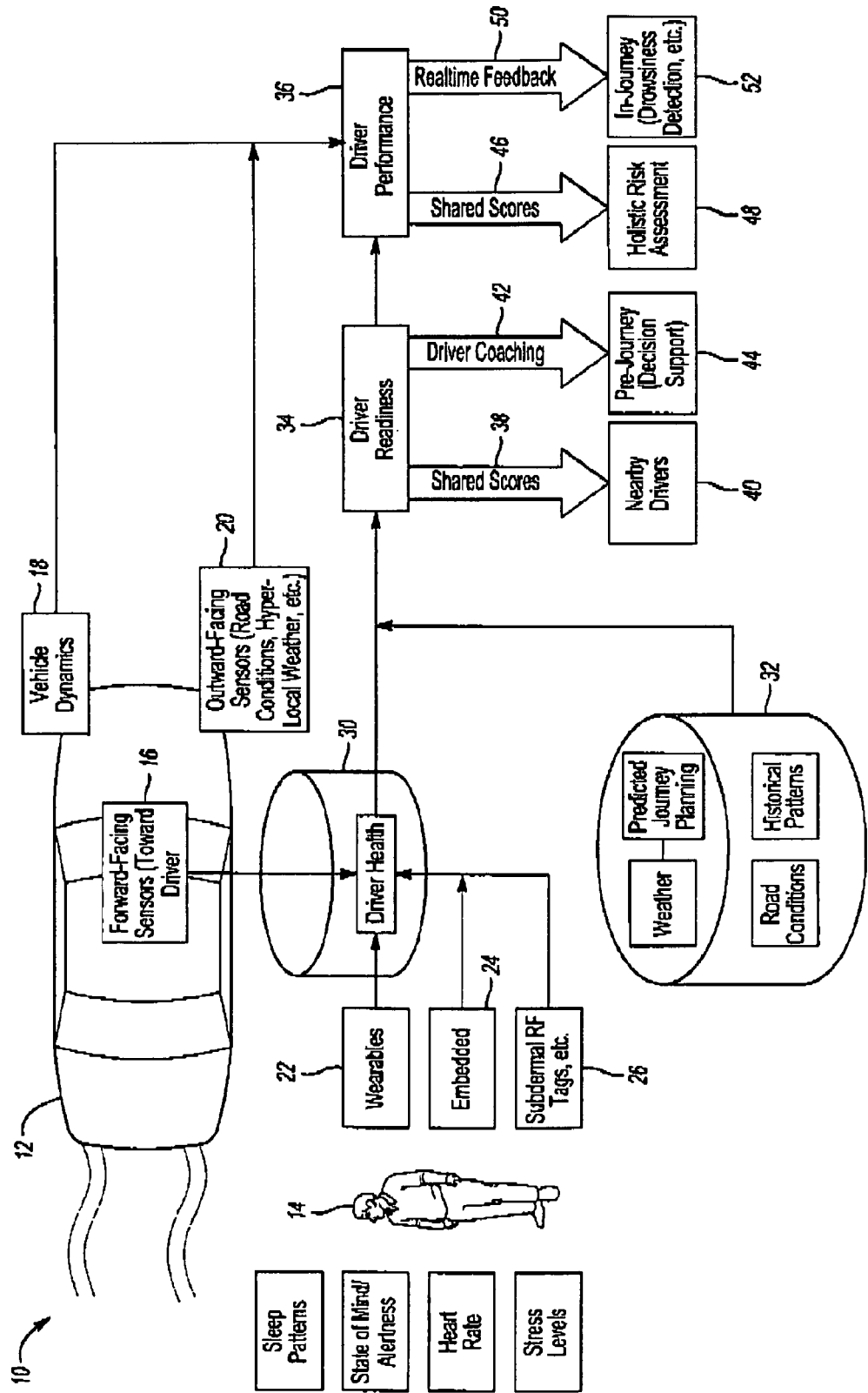

DRIVER READINESS AND INTEGRATED PERFORMANCE ASSESSMENT

BACKGROUND

Traditional vehicle safety systems focus on vehicle health and the operational status of key components including steering, engine temperature, and electronic stability control. In recent vehicles, these safety systems extend beyond the vehicle to include proximity detection for parking aids, adaptive cruise control, and driver assisted braking, steering, and parking features. While these systems are valuable to detect failures and hazardous conditions, they have very limited information about the health of the person behind the wheel beyond select systems that assess driver focus from gaze.

Assessing and understanding the health of the person behind the wheel is just as important, if not more important than monitoring the health of the vehicle itself. With a proper understanding of the health of the driver, the driver can be notified before the journey begins about potential risks to ensure they make informed decisions, the vehicle can help compensate or engage fail-safe measures when the driver becomes drowsy, distracted, or unfocused, and effective measures can be taken to reduce incidents caused by driver error.

SUMMARY

A driver assessment system includes at least one vehicle sensor on a vehicle gathering vehicle dynamics information. At least one occupant sensor gathers driver information. The at least one occupant sensor may be a wearable device or subdermal device on the driver. At least one computer receives the vehicle dynamics information and the driver information to determine a driver readiness.

BRIEF DESCRIPTION OF THE DRAWINGS

FIG. 1 is a schematic of a driver readiness and integrated performance assessment system according to one embodiment.

DETAILED DESCRIPTION

A driver readiness and integrated performance assessment system 10 is shown schematically in FIG. 1. The system 10 is integrated with a vehicle 12 to be driven by driver 14. Inward-directed sensors 16 (that is, directed toward the driver 14) are installed in the vehicle 12. The inward-directed sensors 16 may include heart rate sensors, skin conductivity sensors, olfactory sensors, etc. The system 10 further includes vehicle dynamics sensors 18 installed on the vehicle 12, such as gps, speed sensor, accelerometers, and any information available on on-board data bus, such as via an OBDII port. Vehicle dynamics includes speed, acceleration (lateral as well as longitudinal, including rate of acceleration/deceleration, rate of lateral acceleration, etc). Outward-directed sensors 20 may also be installed on the vehicle 12, such as road condition sensors, externally-facing cameras, microphones, hyper-local weather sensors, etc.

The system 10 may further include wearable sensors 22, such as watches or wristbands with vibro/tactile sensors, heart rate sensors, etc, such as Fitbit® or Apple Watch or the like. The system 10 may further include embedded human technologies 24, including pacemakers with wireless access. The system may further include subdermal devices 26, such as RF tags, etc.

An on-board device 30 includes a computer having a processor and memory and/or storage, wireless communication circuitry (e.g. cell phone/4GLT connection or the like), local wireless connectivity (e.g. Bluetooth). The on-board device 30 receives information from the inward-directed sensors 16, vehicle dynamics sensors 18, the outward-directed sensors 20, the wearable sensors 22, embedded human technologies 24, subdermal devices 26 via the local wireless connectivity. The on-board device 30 receives (or can determine) sleep patterns, state of mind/alertness, heart rate and stress levels of the driver 14 from the wearable sensors 22, embedded human technologies 24 and subdermal devices 26.

The on-board device 30 also receives external information from external servers (computers with processors, memory and storage) that supply weather, predicted journey planning, road conditions, historical patterns of the driver, etc.

The on-board device 30 uses all of this information to determine driver readiness 34. Driver readiness 34 may be shared with nearby drivers 40 (via wifi or the internet or via the server 32). The driver readiness 34 may also factor into driver coaching 42. The driver readiness 34 in combination with the vehicle dynamics information from vehicle dynamics sensors 18 can be used by the on-board device 30 to create shared scores 46 that factor into holistic risk assessment 48 (such as for calculating insurance rates). The driver readiness 34 in combination with the vehicle dynamics information from vehicle dynamics sensors 18 can also be used by the on-board device 30 to give realtime feedback 50 to the driver 14 in-journey 52 (for example, to give wake-up alerts to the driver 14 based upon a detection of drowsiness of the driver 14).

The disclosed system 10 and method leverage driver health and lifestyle behavior with contextual information and predicted and current travel plans to prepare the driver 14 for their journey, inform the driver 14 to help influence smart decisions, and deliver a holistic solution to driver and transportation safety.

Holistic Lifestyle Assessment: Driver lifestyle is monitored to assess current state of mind, level of alertness, focus, and/or predict state of mind throughout future journeys. This monitoring aspect is important to help determine underlying characteristics of the driver 14 that may not be immediately externally observable, but still contribute to driver 14 decision-making processes. Elements of driver 14 lifestyle assessed include but are not limited to:

Sleep patterns—did the driver get sufficient sleep recently?

Dietary habits—is the driver consuming a well-balanced diet? Are their blood-sugar levels within a good range?

Stress levels—is the driver experiencing abnormal levels of stress?

Exercise patterns—is the driver in good physical condition?

Social interaction—does the driver maintain healthy relationships? Are there psychological implications that need to be considered?

Integrated Human Health Sensing: Integration with wearable devices 22 and/or subdermal technologies 26 provides an existing channel to gather health and performance information through from body-equipped sensors. This information is combined with information gathered from the use and movement of portable devices (e.g. cell phones or smart phones when in pockets, etc.), vehicle-equipped sensors (built-in, or aftermarket), and external sensors to derive a comprehensive representation the driver's health at any point in time. Some of these measured items include:

Measurement of heart rate to detect anomalous heart rate conditions. For example, sudden changes, or very low heart rates indicative of a drowsy driver. Near misses, or near accidents can also cause sudden changes in the driver's heart rate but may not be easily detected based on vehicle dynamics or other factors. The on-board device 30 may ignore sudden changes in the driver's heart rate that appear to have been caused by a near-accident, as evidenced by the vehicle dynamics sensors 18.

Blood-sugar levels, as determined by the wearable devices 22 or subdermal devices 26 can assess dietary health and chemical balance.

Sleep patterns, and changes or anomalies in sleep patterns, are an input from the wearable devices 22 or subdermal devices 26 to determine or predict driver alertness.

Passive or active blood-alcohol measurements from the wearable devices 22 or subdermal devices 26 are input to the on-board device 30.

Olfactory sensors—when was the last time the driver had a shower? Poor personal hygiene can be an indicator of a poor mental and/or poor physical state of the driver 14.

Skin conductivity, as determined by wearable devices 22 or subdermal devices 26 or inward-looking sensors 16, can be used a proxy for stress levels. The stress level of the driver 14 is a factor considered by the on-board device 30.

Automatic identification chip measurement (i.e. Pet RFID tags) are read by inward-directed sensors 16 to determine who, how many or what (i.e. pets) are in the vehicle 12.

Embedded human technologies 24 include pacemakers with wireless access.

Proactive Driver Feedback: The system 10 employs flexible feedback and alerting mechanisms that employ configurable and/or trainable escalation paths that can occur concurrently, or sequentially with optional conditions on specific activities. Examples include minimizing the duration of time in which the driver 14 is drowsy by using initial feedback in a vibro/tactile manner on a wristband or other wearable device 22. If the driver continues to exhibit drowsy symptoms, the vehicle 12 can be configured to escalate this feedback in an audible manner, followed by applying vibrational feedback from the seat itself, or even climate control feedback to adjust the environment in an effort to improve driver focus. Some of the triggers available in the escalation paths include:

Use of vibro/tactile feedback using wearable technologies 22.

Use of steering wheel vibro/tacticle feedback.

Contextually relevant audible or spoken feedback.

Delivery of feedback via text message, email, etc.

Voice call (optionally automated) to designated recipient(s).

Broadcasted messages via social media.

Internal climate adjustments.

Notification with a call center or public safety answering point (PSAP) for assistance.

Journey Prediction: The system 10 includes a prediction module to predict future journeys based on historical driving habits, time of day, location, dietary patterns, social interaction, and other behavioral cues in combination with driving behavior. Predicted future journey paths (including timing) are used to both prepare the vehicle 12 in anticipation of the driver's arrival (climate preconditioning, seat warming, etc.), and also to assess travel readiness given both the state of the driver 14, and the impact of the predicted journey ahead. The driver's readiness for a short commute may be very different from the driver's readiness for a two day road trip.

Journey Planning: In this system 10, journeys can be planned by incorporating driver 14 health information to optimize routes. This approach uses more than the traditional elements of distance, time, and fuel efficiency to also incorporate appropriate rest stops and paths to minimize overall driver risk and maintain a desired driver readiness score throughout one or more journeys.

Driver Readiness Score: Assessment of travel readiness using multiple cues including predicted hyper-local weather along the journey ahead, road conditions, state of charge or fuel level in the vehicle, and driver 14 state of mind and predicted state throughout the journey. Travel readiness is summarized into a score (a number from 0-100) with coaching guidance for the driver 14. The driver 14 has the option to review individual contributing factors that roll into the overall readiness score. Driver 14 readiness information can be accessed on demand from any computer or mobile device, in addition to being pushed to the driver in an unsolicited manner when the system 10 determines that the driver 14 is getting ready for a journey (i.e. by approaching their vehicle, or based on historical behavioral patterns).

Shared Readiness and Accessibility: Information about driver 14 readiness can be exposed to nearby travelers. This level of transparency helps other travelers on the road avoid or drive more cautiously around a driver 14 with a low readiness score even before that driver 14 might exhibit symptoms. The aggregate set of driver 14 readiness scores for vehicles 12 on any given road segment can also be used to influence the expected risk level associated with driving through the given road segment.

Driver Risk Assessment: Since information about the driver's health and driving behavior is available in this system 10, an overall risk assessment can be derived, beyond traditional driving risk assessments employed in recent usage-based-insurance programs. This approach involves ranking and/or scoring the driver 14 using an element of driving behavior, an element of demographics, and an element of health to derive a precise model for individual driver risk. This measure is important across many applications including combined health, life, and automotive insurance.

Enhanced Emergency Assistance and First Notice of Loss: Use of occupant health information to proactively inform first responders and emergency services personnel about the total occupants within the vehicle, their characteristics (male/female, child/adult, etc.), and health information that may be important to ensure sufficient medical equipment, blood, and other items are made available.

As an alternative, some or all of the information gathering, determinations, calculations and warnings could be performed on the server 32 instead of on the on-board device 30. Alternatively, some tasks could be performed by the on-board device 30 while others are performed on the server 32.

In accordance with the provisions of the patent statutes and jurisprudence, exemplary configurations described above are considered to represent a preferred embodiment of the invention. However, it should be noted that the invention can be practiced otherwise than as specifically illustrated and described without departing from its spirit or scope.

What is claimed is:

1. A driver assessment system comprising:
at least one vehicle sensor on a vehicle gathering vehicle dynamics information;
at least one occupant sensor gathering driver information regarding a driver of the vehicle, wherein the at least one occupant sensor is a wearable device or subdermal device on the driver; and
at least one computer receiving the vehicle dynamics information and the driver information to determine a driver readiness, wherein the at least one computer determines driver readiness in light of a length of an expected journey, wherein the at least one computer implements proactive, escalating driver feedback based upon the driver readiness determination.

2. The system of claim 1 further including at least one inward-directed sensor in the vehicle, the at least one computer receiving additional driver information from the inward-directed sensor.

3. The system of claim 1 wherein the at least one computer determines driver performance based upon the vehicle dynamics information and the driver information.

4. The system of claim 1 wherein the at least one computer determines driver readiness based upon heartbeat measured by the at least one occupant sensor.

5. The system of claim 1 wherein the at least one computer determines driver readiness based upon sleep patterns, as determined by the at least one occupant sensor.

6. The system of claim 1 wherein the at least one computer determines driver drowsiness based upon the driver information.

7. The system of claim 6 wherein the at least one computer determines the driver drowsiness based upon heart rate from the at least one occupant sensor.

8. The system of claim 7 wherein the at least one computer transmits the driver readiness determination to nearby drivers in other vehicles.

9. The system of claim 1 wherein the driver readiness determination is transmitted to a server, the server compiling driver readiness determinations from a plurality of vehicles on a road segment including the vehicle and assessing a risk level on the road segment based upon the driver readiness determinations.

10. The system of claim 1 wherein the at least one computer determines driver drowsiness as part of the driver readiness determination.

11. The system of claim 1 wherein the proactive, escalating driver feedback is given via vibro/tactile feedback on the at least one occupant sensor and wherein the at least one occupant sensor is a wearable device.

12. The system of claim 1 wherein the driver readiness determination and vehicle dynamics information is used to determine a driver risk assessment for determining a rate of insurance.

13. A method for assessing driver readiness including the steps of:
receiving driver information from at least one occupant sensor before an expected journey begins;
receiving journey information regarding the expected journey, including a length of the expected journey;
determining driver readiness before the expected journey begins based upon the driver information in light of the length of the expected journey; and
incorporating rest stops into the expected journey based upon the driver readiness.

14. The method of claim 13 wherein the step of determining driver readiness is based upon sleep information of the driver.

15. The method of claim 14 further including the step of receiving the sleep information from the at least one occupant sensor and wherein the at least one occupant sensor is a wearable device or a subdermal device.

16. A method for assessing driver readiness including the steps of:
receiving driver information from at least one occupant sensor;
receiving vehicle dynamics information from at least one vehicle sensor on a vehicle;
determining driver readiness before an expected journey begins based upon the driver information in light of a length of the expected journey and based upon the vehicle dynamics information;
sharing the driver readiness with nearby drivers in different vehicles; and
aggregating driver readiness for a plurality of drivers of a plurality of vehicles including the vehicle on a road segment and determining a risk level associated with the road segment based upon the aggregated driver readiness.

17. The method of claim 16 wherein said step of sharing includes sharing the driver readiness via a wireless network.

18. The system of claim 1 wherein the proactive, escalating driver feedback is given via vibro/tactile feedback on the at least one occupant sensor.

19. The system of claim 1 wherein the at least one occupant sensor is a wearable device.

20. The system of claim 19 wherein the driver readiness determination and vehicle dynamics information is used to determine a driver risk assessment for determining a rate of insurance.

21. The system of claim 1 wherein the at least one computer is configured to incorporate rest stops into the expected journey based upon the driver readiness.

22. The method of claim 13 wherein the steps are performed by at least one computer.

23. The method of claim 22 further including the step of implementing proactive, escalating driver feedback based upon the driver readiness determination.

24. The method of claim 23 wherein the at least one occupant sensor is a wearable device.

25. A method for assessing driver readiness including the steps of:
receiving driver information from at least one occupant sensor before an expected journey begins;
receiving journey information regarding the expected journey, including a length of the expected journey;
determining driver readiness before the expected journey begins based upon the driver information in light of the length of the expected journey; and
implementing proactive, escalating driver feedback based upon the driver readiness determination.

26. The method of claim 25 wherein the steps are performed by at least one computer.

27. The method of claim 26 wherein the at least one occupant sensor is a wearable device.

* * * * *